US011897838B2

(12) United States Patent
Cheng et al.

(10) Patent No.: US 11,897,838 B2
(45) Date of Patent: Feb. 13, 2024

(54) HIGH-PURITY ISOTHIOCYANATE COMPOUND PREPARATION METHOD FOR INDUSTRIAL PRODUCTION

(71) Applicant: JC (WUXI) COMPANY, INC., Wuxi (CN)

(72) Inventors: Jingcai Cheng, Wuxi (CN); Guolin Gu, Wuxi (CN); Biao Huang, Wuxi (CN)

(73) Assignee: JC (WUXI) COMPANY, INC., Jiangsu (CN)

( * ) Notice: Subject to any disclaimer, the term of this patent is extended or adjusted under 35 U.S.C. 154(b) by 334 days.

(21) Appl. No.: 16/489,226

(22) PCT Filed: Feb. 27, 2018

(86) PCT No.: PCT/CN2018/077443
§ 371 (c)(1),
(2) Date: Nov. 26, 2019

(87) PCT Pub. No.: WO2018/153381
PCT Pub. Date: Aug. 30, 2018

(65) Prior Publication Data
US 2020/0079731 A1 Mar. 12, 2020

(30) Foreign Application Priority Data
Feb. 27, 2017 (CN) .......................... 201710108328.9

(51) Int. Cl.
C07C 331/20 (2006.01)
C07C 331/24 (2006.01)

(52) U.S. Cl.
CPC .......... *C07C 331/20* (2013.01); *C07C 331/24* (2013.01)

(58) Field of Classification Search
None
See application file for complete search history.

(56) References Cited

FOREIGN PATENT DOCUMENTS

| CN | 1880302 | A | 12/2006 |
|---|---|---|---|
| CN | 101759614 | A | 6/2010 |
| CN | 102229551 | A | 11/2011 |
| CN | 103102296 | A | 5/2013 |
| CN | 103360282 | A | 10/2013 |
| CN | 103833780 | A | 6/2014 |
| CN | 104072395 | A | 10/2014 |
| CN | 105797771 | * | 7/2016 |

OTHER PUBLICATIONS

Chemical Abstract Registry No. 57-06-7, indexed in the Reigstry File ON STN CAS Online Nov. 16, 1984.*
The machined-generated English translation of Foreign Patent Application Publication No. CN1880302, published on Dec. 20, 2006.*
Machine generated English translation of Foreign Patent Publication No. CN105797771, published on Jul. 27, 2016.*
CAPLUS printout of Foreign Patent Publication No. CN105797771, published on Jul. 27, 2016.*
International Search Report and Written Opinion, International Patent Application No. PCT/CN2018/077443, dated May 31, 2018, with English translation of Search Report (14 pages).

* cited by examiner

*Primary Examiner* — Po-Chih Chen
(74) *Attorney, Agent, or Firm* — HAMRE, SCHUMANN, MUELLER & LARSON, P.C.

(57) ABSTRACT

The present invention provides a high-purity isothiocyanate compound preparation method for industrial production. Specifically, in the method, organic amine and CS2 are used as raw materials to prepare the thiocarbamate, and then desulfurization is carried out, and the high-purity isothiocyanate compound is obtained by using purification, post-processing and other methods. The method in the present invention is suitable for industrial production, is simple in the post-processing, has a high yield rate, and allows the product to have a high purity, and is suitable for the production of the isothiocyanate compound in the pharmaceutical industry.

14 Claims, 8 Drawing Sheets

HIGH-PURITY ISOTHIOCYANATE COMPOUND PREPARATION METHOD FOR INDUSTRIAL PRODUCTION

FIELD OF THE INVENTION

The present invention relates to a process for the preparation and purification of high-purity isothiocyanate compound which is applicable in industrial production.

BACKGROUND OF THE INVENTION

Isothiocyanates are very important functional substances in natural products and pharmaceutically active compounds which is of the structural formula RN=C=S, as well as an important type of organic synthesis intermediates. They have a wide range of applications in mineral processing, medicine, pesticides and dyes. They can be used in medicine for antibacterial, anti-inflammatory and prevention and treatment of cancer; and can be used in agriculture as antibacterial agent, insecticide or herbicide. In addition, isothiocyanates can also participate in a variety of organic reactions for the synthesis of various types of compounds (especially heterocyclic compounds) containing sulfur, nitrogen, oxygen, and are widely used in the production of pesticides, medicine, dyes and other organic synthetic products. They can also be used to determine the amino acid sequence in peptides and proteins, or used as fluorescein markers.

Since having a good medicinal prospect, researches on the drug activity of isothiocyanates is very active at home and abroad, which. Research on the application of cruciferous vegetable containing isothiocyanate compound in the cancer chemoprevention has continued for forty years. More than 20 epidemiological studies covering lung cancer, breast cancer, prostate cancer, bladder cancer, stomach cancer, colorectal cancer and kidney cancer have shown that the intake of cruciferous vegetables containing isothiocyanate compound is negatively correlated with the risk of multiple cancer prevalence. At present, isothiocyanates have been approved for clinical use in the United States or China in the prevention of lung cancer, prostatic hyperplasia and oral cancer in healthy people.

Therefore, the development of preparation methods for the isothiocyanate compound, especially with high-purity, pharmaceutical-compliant, and applicable for industrial production is particularly urgent. At present, there are many reported synthesis methods for isothiocyanates, including phosgenation, thiophosgenation, carbon disulfide method, bis(trichloromethyl) carbonate method, thiourea decomposition method, phenyl thiochloroformate method and thiocyanate method, etc, of which the most widely used is:

Phosgenation route: Hodgkius et al. reported that phenethylamine and carbon disulfide were dissolved in organic solvent, and then phosgene was introduced in the presence of base to form phenethyl isothiocyanate. The phosgene herein can also be replaced by phosgene substitutes such as ethyl chloroformate, diphosgene, triphosgene, and the like. However, this reaction process still cannot avoid the formation of phosgene, which is easy to pollute the environment and has a great potential safety hazard.

Thiophosgenation route: thiophosgene reacts directly with amine compounds to produce isothiocyanates. This route is widely used and the reaction was rapid, and safety was improved since thiophosgene is used instead of phosgene. However, thiophosgene is a toxic and volatile liquid with great damage to environment, thus being unsafe for production and transportation. Therefore this route is disadvantage for large-scale industrial production;

Isonitrile route: in the presence of metal catalyst, the isothiocyanate is synthesized from isonitrile and sulfur powder or vulcanizing agent. The main problem of this route lies in the difficulty of synthesis and purification of isonitrile, and the isonitrile itself is also a highly toxic substance, which cannot be used in industrial production.

Thiocyanate route: halohydrocarbon reacted with thiocyanate to produce isothiocyanates. The yield of this route is low and the operation is complicated.

Carbon disulfide route: the raw materials such as phenethylamine (or other amine organic matter) and carbon disulfide were dissolved in organic solvent, and the amine dithioformate were synthesized under the catalysis of base, then the isothiocyanate compounds were obtained in the presence of desulfurizing agent. There are many researches on the selection of desulfurizers, mainly includes methyl chloroformate, p-toluenesulfonyl chloride, solid phosgene, elemental iodine, chlorosilane, chlorophosphate or dicyclohexylcarbodiimide. This method has the advantages of avoiding the use of highly toxic raw materials; however, the target product produced was of many impurities, which makes the product of low purity. The product was generally purified by silica gel chromatography column, which is complicated to operate and would consume large amount of reagent, which makes it suitable for only experimental level reaction instead of industrial production.

US2859235A discloses a process for producing N-monosubstituted dithiocarbamic acid with alkaline hypohalite solution.

In view of this, there is an urgent need to develop a method for preparing and purifying isothiocyanate compound which will be safe, simple, environmental friendly and can be used in industrially production to provide isothiocyanate compound of high-purity and high-quality so as to satisfying the growing medicinal and industrial production needs.

SUMMARY OF THE INVENTION

The object of the present invention is to provide a process for the preparation and purification of isothiocyanate compounds which will be safe, simple, environmental friendly and enable to implement industrial production.

In the first aspect of the invention, a process for the preparation of an isothiocyanate compound of formula (I) is provided,

A-N=C=S     (I)

in formula I:
—N=C=S is isothiocyanate group;
A is —$XR_1$ or —$CR_2R_3R_4$, wherein
X is —$(CH_2)_n$—, and n is an integer of 0-6;
$R_1$ is selected from the group consisting of methyl, tert-butyl, isopropyl, methylthio, methoxy, allyl, methallyl, cyclohexyl, methylsulfinyl, naphthyl, methyl cyclohexyl, morpholinyl, diethylamino, benzoyl, ethoxycarbonyl, tert-octyl, chlorine, trimethylsilyl, substituted or unsubstituted phenyl;
wherein, the "substituted" means that one or more hydrogen in the group are substituted by substituents selected from the following group: halogen, methyl, bromomethyl, ethyl, methoxy, nitro, azido, trifluoromethyl, difluoromethoxy, methylthio, cyano, trifluoromethoxy, trifluoromethylthio, tert-butoxycarbonyl, ethoxycarbonyl;

$R_2$, $R_3$, and $R_4$ are each independently H, phenyl or $C_{1-3}$ alkyl;

wherein the process comprises the following steps:

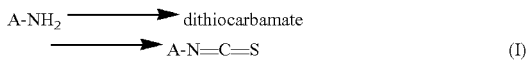

$$A\text{-}NH_2 \longrightarrow \text{dithiocarbamate} \longrightarrow A\text{-}N\!=\!C\!=\!S \quad (I)$$

(1) in the presence of organic base, $ANH_2$ reacts with $CS_2$ in organic solvent to obtain a first reaction mixture containing dithiocarbamate;

(2) in the presence of an optional base catalyst, adding desulfurizing agent to the first reaction mixture to carry out a desulfurization reaction so as to obtain a second reaction mixture containing isothiocyanate compound;

(3) the second reaction mixture is purified by post-processing to obtain the isothiocyanate as shown in formula (I).

In another preferred embodiment, the step (1) comprises: adding $ANH_2$ drop wise to the reaction system to which $CS_2$ is added for reaction.

In another preferred embodiment, in the step (1), the organic solvent is capable of dissolving phenethylamine and dithiocarbamate and immiscible with water; preferably, the organic solvent is selected from the group consisting of ethyl acetate, isopropyl acetate, methyl propionate, ethyl propionate, butyl acetate, isobutyl acetate, amyl propionate, butanol, isobutanol, pentanol, sec-pentanol, tert-pentanol, 3-methyl-2-butanol, hexanol, heptanol, dichloromethane, dichloroethane, chloroform, diethyl ether, petroleum ether, cyclohexane, or the combinations thereof.

In another preferred embodiment, in the step (1), the organic base is selected from the group consisting of triethylamine, trimethylamine, diisopropylethylamine, triethylene diamine, pyridine, 4-N,N-dimethyl pyridine, potassium t-butoxide, sodium methoxide, sodium ethoxide, hydroxylamine, 3-methylpyridine, pyrrole, or the combinations thereof.

In another preferred embodiment, in the step (2), the desulfurizing agent is selected from the group consisting of methyl chloroformate, p-toluenesulfonyl chloride, solid phosgene, elemental iodine, chlorosilane, chlorophosphate, dicyclohexylcarbodiimide, dicyandiamide, triphenylphosphine, di-tert-butyl dicarbonate, cyanuric chloride, or the combinations thereof.

In another preferred embodiment, in the step (2), the base catalyst is selected from the group consisting of triethylamine, triethylenediamine, pyridine, 4-dimethylaminopyridine, or the combinations thereof.

In another preferred embodiment, in the step (1), the organic amine and triethylamine were added into ethyl acetate solvent, the temperature of the mixture was controlled to be T1, and the carbon disulfide/ethyl acetate mixture was slowly added dropwise by stirring. The temperature of the reaction liquid was controlled to be T2. After the completion of the dropwise addition, the temperature of the reaction liquid was controlled to be T3 to react for 0.5-2 h.

In another preferred embodiment, the temperature T1 in the step (1) is 0° C.-30° C., preferably 0° C.-20° C., more preferably 0° C.-5° C., and the temperature T2 is 0° C.-40° C., preferably 0° C.~30° C., more preferably 10° C.~25° C.; and the temperature T3 is 0° C.~40° C., preferably 10° C.~30° C.;

In another preferred embodiment, the step (2) includes controlling temperature at T4, adding desulfurizing agent and base catalyst into the reaction liquid, and then the reaction was stirred to react at a temperature T5, and the reaction was completed within 1-4 h.

In the second step, the temperature T4 is 0° C.-30° C., preferably 0° C.-20° C.; the temperature T5 is 0° C.-50° C., preferably 10° C.-30° C., more preferably 20° C.-30° C.

In another preferred embodiment, in the step (1), the ratio of the $ANH_2$ to the carbon disulfide is 1:1.0-10, preferably 1:1.0-5, more preferably 1:1.05-2;

The ratio of the $ANH_2$ to the organic base is 1:0.5-5, preferably 1:0.8-3, more preferably 1:0.9-2; the mass volume ratio of the $ANH_2$ to the ethyl acetate is 10-25%;

In another preferred embodiment, in the step (2), the ratio of the $ANH_2$ to the desulfurizing agent in the first step is 1:0.9-5, preferably 1:0.9-2, more preferably 1:0.95-1.5;

The mass ratio of the base catalyst to the $ANH_2$ in the first step is 0-4 wt %, preferably 0.01-2 wt %, more preferably 0.05-1 wt %.

In another preferred embodiment, in the step (3), the post-processing purification method comprises the steps of:

washing the second reaction mixture, and concentrating to obtain an acid washed crude product;

distilling acid washed crude product to obtain a distilled crude product containing isothiocyanate; preferably, the distillation is reduced pressure distillation;

the distilled crude product is subjected to rectification under vacuum to obtain a pure isothiocyanate product.

In another preferred embodiment, the washing step comprises: washing with an acid solution, wherein the molar ratio of the total amount of the acid in the acid solution to the organic base added in the step (1) is 0.8-5:1, preferably 0.9-2:1, more preferably 1-1.5:1 (calculated as monobasic acid and monobasic base).

In another preferred embodiment, the volume of wash liquor is 20-100%, preferably from 25-50% by volume of the organic phase per wash.

In another preferred embodiment, in the post-processing purification, the concentration temperature is 30° C.~90° C., preferably 35° C.~60° C.;

In another preferred embodiment, the post-processing purification comprises collecting the corresponding isothiocyanate fractions based on the boiling points of the different isothiocyanates.

In another preferred embodiment, in the post-processing purification, the pressure of reduced pressure distillation and rectification is 10-1000 Pa, preferably 10-500 Pa.

In another preferred embodiment, the post-processing purification comprises one or more characteristics selected from the group consisting of:

the rectification under vacuum is continuous rectification or batch rectification, preferably batch rectification;

the rectifying column adopts structured packing or random packing. Preferably, the structured packing is selected from the group consisting of corrugated packing or grid packing; the random packing is selected from the group consisting of Pall ring packing, Raschig ring packing, flat ring packing, cascade packing ring, intalox saddles packing, octagonal ring packing, conjugate ring packing, Teller Rosette packing, HY-PAK packing, Dixon ring packing, Cannon ring packing, Triangular spiral ring packing, spherical packing, or the combinations thereof; or in the post-processing purification, the rectified packing material is selected from the group consisting of stainless steel, plastic, glass, ceramic, or the combinations thereof; preferably, the rectified packing material is selected from the group consisting of stainless steel, ceramics, or the combinations thereof.

In another preferred embodiment, in the reduced pressure rectification process, the reflux ratio of the front fraction is 99:1-1:99 (preferably 99:1-50:50, more preferably 90:10-70:30);

the reflux ratio of the middle fraction is 99:1-1:99 (preferably 90:10-10:90, more preferably 70:30-30:70);

the reflux ratio of the post-fraction is 99:1-1:99 (preferably 99:1-50:50, more preferably 90:10-70:30).

In another preferred embodiment, in the post-processing purification, the purity of the distilled crude product is greater than 95%, preferably greater than 97%; the purity of the rectified pure product is greater than 99.0%, preferably greater than 99.6%.

In another preferred embodiment, the post-processing purification method comprises the steps of: washing the reaction solution with a hydrochloric acid solution, repeating twice; washing the organic phase with saturated brine, and repeating washing to neutral (pH 6-7); and then drying the organic phase with anhydrous sodium sulfate; filtering the mixture and evaporating the filtrate to dryness under reduced pressure to obtain a crude product; washing the crude product with acid, and reduced pressure distillating by using a rotary vane vacuum pump or a vacuum unit to collect the isothiocyanate fraction to obtain a crude distillation product; full reflux distilling the crude product by using a two-stage rotary vane vacuum pump or vacuum unit; after the reflux was stabilized, setting appropriate reflux ratio to collect pure isothiocyanate.

In a second aspect of the invention, equipment for producing isothiocyanate compound is provided, which comprises:

a main reactor for performing main reaction, acidic water washing reaction, and concentration operation;

a crude distillation kettle located downstream of the main reactor, and the crude distillation kettle is used for distillation of concentrated products;

a rectification column for rectifying the crude obtained by the distillation.

In another preferred embodiment, the apparatus further includes one or more feeding tanks connected to the main reactor.

In another preferred embodiment, the apparatus further comprises: a first condenser located between the main reactor and the rectification column, a second condenser and a third condenser located between crude distillation kettle and the rectification column.

It should be understood that, in the present invention, each of the technical features specifically described above and below (such as those in the examples) can be combined with each other, thereby constituting new or preferred technical solutions which need not be specified again herein.

DESCRIPTION OF THE DRAWINGS

FIG. 2-1: HPLC chromatogram (208nn) for purity test of phenethyl isothiocyanate;

FIG. 2-2: HPLC chromatogram (244nn) for purity test of phenethyl isothiocyanate;

EMBODIMENTS FOR CARRYING OUT THE INVENTION

Figure 1:
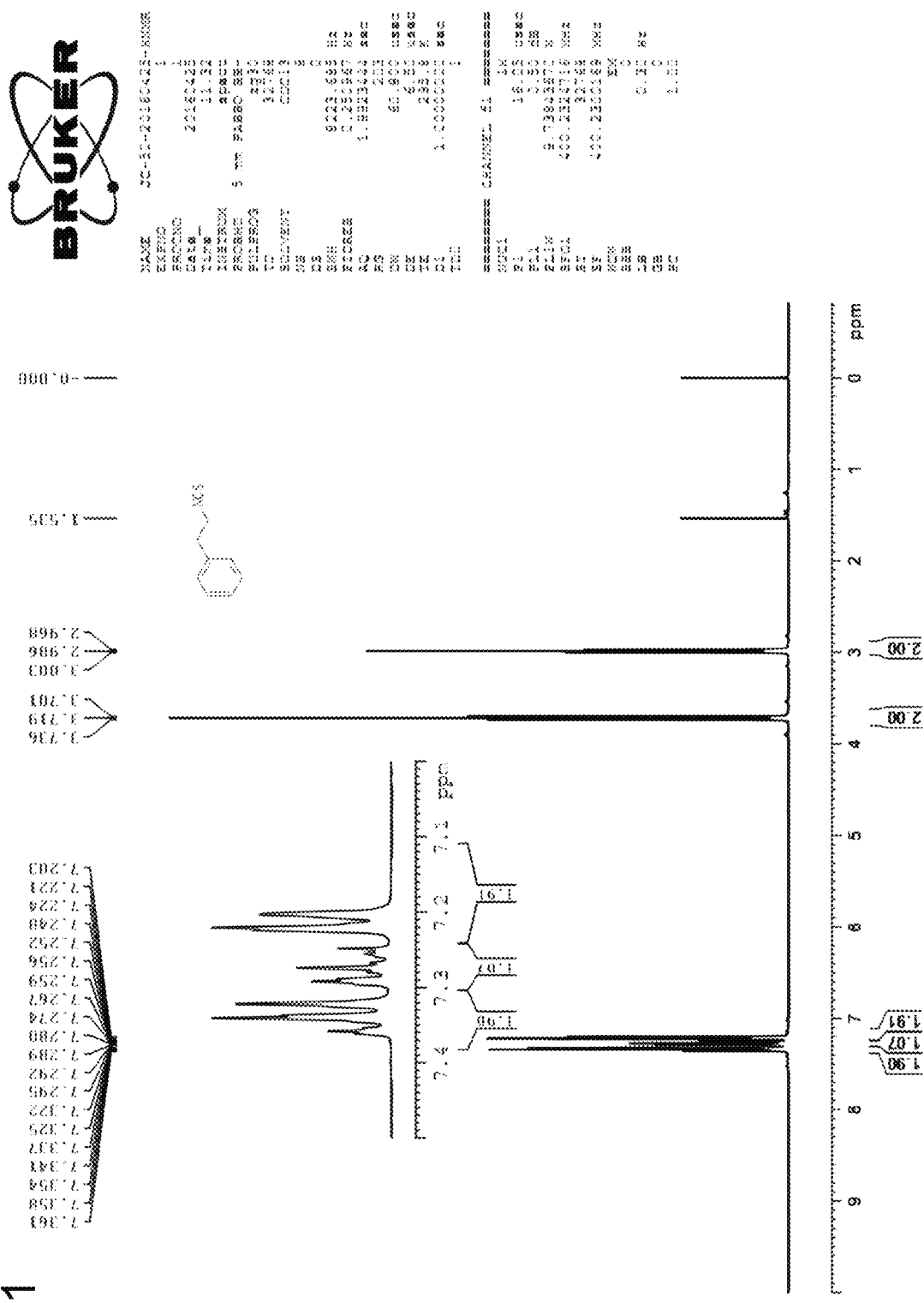
FIG. 1: the structure-confirmation $^1$H NMR pattern of phenethyl isothiocyanate.

Through long-term and intensive study, the inventors have provided a one-pot method for preparing isothiocyanates. The method of the invention is safe, simple, environmental friendly, and can be used in industrial production. Moreover, the post-processing purification of the method is simple, and the obtained isothiocyanate compound is of high-purity, thus being qualified for medical demands. Based on the above findings, the inventors completed the present invention.

Preparation of Isothiocyanate Compound

The invention provides a preparation method of isothiocyanate compounds, the method comprises the steps of:

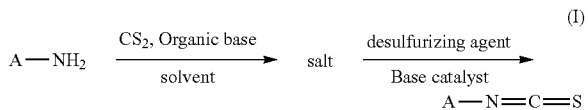

(I)

in formula I:

N=C=S is isothiocyanate group;

A is —XR$_1$ or —CR$_2$R$_3$R$_4$, wherein

X is —(CH$_2$)$_n$—, and n is an integer of 0-6;

R$_1$ is selected from the group consisting of methyl, tert-butyl, isopropyl, methylthio, methoxy, allyl, methallyl, cyclohexyl, methylsulfinyl, naphthyl, methyl cyclohexyl, morpholinyl, diethylamino, benzoyl, ethoxycarbonyl, tert-octyl, chlorine, trimethylsilyl, substituted or unsubstituted phenyl;

wherein, the "substituted" means that one or more hydrogen in the group are substituted by substituents selected from the group consisting of halogen, methyl, bromomethyl, ethyl, methoxy, nitro, azido, trifluoromethyl, difluoromethoxy, methylthio, cyano, trifluoromethoxy, trifluoromethylthio, tert-butoxycarbonyl, ethoxycarbonyl;

R$_2$, R$_3$, and R$_4$ are each independently H, phenyl or C$_{1-3}$ alkyl.

(1) in the presence of organic base, ANH$_2$ reacts with CS$_2$ in organic solvent to obtain a first reaction mixture containing dithiocarbamate;

(2) in the presence of an optional base catalyst, desulfurizing agent is added to the first reaction mixture to carry out a desulfurization reaction and obtain a second reaction mixture containing isothiocyanate compound;

(3) purifying the second reaction mixture by post-processing to obtain the isothiocyanate as shown in formula (I).

In the step (1), there are no special restrictions on the solvent system. A solvent that can dissolve phenethylamine and dithiocarbamate and is not miscible with water can be used. Preferably, solvents such as, ethyl acetate, isopropyl acetate, methyl propionate, ethyl propionate, butyl acetate, isobutyl acetate, amyl propionate, dichloromethane, dichloroethane, chloroform, diethyl ether, petroleum ether, and cyclohexane are used to reduce the generation of specific impurities and increase the reaction rate, thereby reducing the difficulty of post-processing.

In the reaction, the type of the reactant (organic base, desulfurizing agent) is not particularly limited, and the preferred organic base is selected from the group consisting of triethylamine, trimethylamine, diisopropylethylamine, triethylene diamine, pyridine, 4-N,N-dimethyl pyridine, potassium t-butoxide, sodium methoxide, sodium ethoxide, or the combinations thereof; more preferably triethylamine; preferably, the desulfurizing agent is selected from the group consisting of methylclhlorofonmate, p-toluenesulfonyl chloride, solid phosgene, elemental iodine, chlorosilane, chlorophosphate, dicyclohexylcarbodiimide, dicyandiamide, triphenylphosphine, di-tert-butyl dicarbonate, cyanuric chloride, or a combination thereof; more preferably di-tert-butyl dicarbonate.

During the reaction, the feed ratio of each reactant can be designed according to the actual situation, taking into account the yield, content, purity and related substances, preferably, the ratio of $ANH_2$:organic base=1:0.5-5, preferably 1:0.8-3, more preferably 1:0.9-2; preferably the ratio of $ANH_2$:carbon disulfide=1:1.0-10, preferably 1:1.0-5, more preferably 1:1.05-2.

In the step (2), the desulfurizing agent is preferably in an amount of 1:0.9~5, preferably 1:0.92-2, more preferably 1:0.95~1.5.

In a preferred aspect of the invention, in the step (1) the carbon disulfide is in excess relative to $ANH_2$.

In the reaction, the preferred temperature of each step is not particularly limited, and a suitable reaction temperature may be employed depending on the actual reaction system.

After completion of the reaction, a series of post-processing including pickling, washing with saturated brine, drying, solvent evaporation, reduced pressure distillation, etc. are carried out in consideration of the formation of the by-products in the reaction. Preferably, the solvent used in the post-processing is the same as the solvent used in the reaction.

In a preferred embodiment of the invention, the post-processing purification method comprises the steps of:

washing the second reaction mixture, and then concentrating to obtain an acid pickling crude product;

the acid pickling crude product is subjected to vacuum distillation to obtain a crude distillation product containing isothiocyanate;

the crude distillation product was subjected to reduced pressure distillation to obtain a pure isothiocyanate product.

The conditions of each post-processing purification step can be designed according to the reaction scale, raw material, etc. which is actually used. Preferably, different reflux ratios are used in the front, middle and post fractions during the reduced pressure rectification. In a preferred embodiment of the invention, the reflux ratio of the front fraction is 99:1-1:99 (preferably 99:1-50:50, more preferably 90:10-70:30); the reflux ratio of the middle fraction is 99:1-1:99 (preferably 90:10-10:90, more preferably 70:30-30:70); the reflux ratio of the post-fraction is 99:1-1:99 (preferably 99:1-50:50, more preferably 90:10-70:30). The purity of the final obtained product is more than 99.7% (yield 80%).

The front fraction in the rectification process refers to the first stage fraction from the start of the fraction receiving, and the receiving amount is 0%-30% (preferably 0%-20%, more preferably 5%-10%) of the substrate;

The middle fraction in the rectification process refers to the second fraction after the completion of the reception of the former fraction, and the receiving amount is 40%-100% (preferably 60%-100%, more preferably 80%-90%) of the substrate;

The post-fraction in the rectification process refers to the third fraction after completion of the reception of the previous fraction, and the receiving amount is 0%-30% (preferably 0%-20%, more preferably 5%-10%) of the substrate.

Compared with the Prior Art, the Advantages of the Present Invention are Mainly Embodied in:

1) The invention adopts one-pot method to prepare isothiocyanate, in which the raw materials required for the reaction are cheap and readily available, and a better reaction condition with high reaction conversion rate, mild conditions, convenient operation, easy purification and environmental friendly is explored;

2) the invention adopts a solvent represented by ethyl acetate with low toxicity, high safety, and the reaction, separation and purification steps are realized without using any other organic solvents, thus greatly reducing the use of organic solvents, the use of solvents of low boiling point and high volatility, thus improving the safety of production and reducing environmental pollution, thus very conducive to industrial production;

3) the invention adopts a purification method of pickling, distillation and rectification to obtain an isothiocyanate compound of high-purity, and the product purity is more than 99.6%. Generally, column chromatography method is used in literature or patents, which requires a large amount of organic solvent as well as cumbersome operation. The purification method of the present invention greatly reduces the use of organic solvents, thus simplifying the operation steps and making it easy to adapt to industrial production.

4) The purity of the isothiocyanate prepared by the invention is greater than 99.6%, which can meet the demand of medicine.

The invention is further illustrated with specific embodiments. It is to be understood that the examples are not intended to limit the scope of the invention. The experimental methods in the following examples which do not specify the specific conditions are usually in accordance with conventional conditions or recommended by the manufacturer. Percentage and portion are calculated by weight unless otherwise stated.

Example 1 Preparation of Phenethyl Isothiocyanate

Phenethylamine (300.0 g, 2.48 mol) and triethylamine (350.6 g, 3.46 mol) were placed in a 5000 mL three-neck round bottom flask, and ethyl acetate (1000 mL) was added, and then the mixture was cooled in an ice bath and mechanically stirred. When the temperature of the mixed solution was dropped to 0° C.-5° C., carbon disulfide (339.2 g, 4.45 mol) was slowly added dropwise by a constant pressure dropping funnel, magnetic stirring as dropping, and the temperature of the reaction liquid was controlled to be less than 30° C. After the dropwise addition was completed, magnetic stirring was carried out for one hour at room temperature (10-30° C.); $BOC_2O$ (535.1 g, 2.45 mol) and DMAP catalyst were added to the reaction solution at this temperature, and then the mixture was stirred to react at 30±2.5° C. for 1.5 h. After the completion of the reaction, the reaction solution was washed twice with acid solution, and the total amount of acid consumed by washing was 1.5 times that of triethylamine, and then washed with a saturated saline solution until neutral. The organic phase was concentrated by rotary evaporation to give an acid pickling crude.

The acid pickling crude was placed in a flask heated by a heating mantle, and a rotary vane vacuum pump was adopted, and a fraction of 130° C.-145° C./10 mmHg was collected to obtain a crude product.

The crude distillation product was placed in a rectifying still. The rectifying column specification was φ30*1000 mm, with stainless dixon packing (φ4×4 mm), 2X-8A model rotary vane vacuum pump, the kettle temperature was kept at 160-200° C. After fully refluxed for 0.5 h, the fractions at 95° C.-110° C./200-600 Pa were collected. The front fraction had a reflux ratio of 90:10; after 0.5 hours, the reflux ratio was 50:50, and the middle fraction was collected; finally, the reflux ratio was 70:30, and the post fraction was collected to obtain phenethyl isothiocyanate product (yield 85%), and then identification and purity check was performed.

Example 2 Structure and Purity Check of Phenylethyl Isothiocyanate

1. Structure Identification Result of H-NMR and Spectrum

The results of the nuclear magnetic test are as follows, which is the same as our target product.

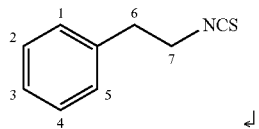

$^1$H NMR (400 MHz, CDCl$_3$) δ 7.37-7.31 (m, 1H), 7.28 (ddd, J=10.2, 5.0, 2.1 Hz, 1H), 7.23-7.19 (m, 1H), 3.72 (t, J=7.0 Hz, 1H), 2.99 (t, J=7.0 Hz, 1H).

Nuclear magnetic detection is shown in FIG. 1.

2. Purity Detection of Phenethyl Isothiocyanate

Instrument conditions: Dionex U3000, C18 bonded silica gel column, 208/244 nm, 1.0 ml/min, column temperature was 30° C., 10 ul of injection sample, and analysis for 30 min;

The mobile phase was with the gradient of 0 min 40% acetonitrile, 15 min 62.5% acetonitrile, 23 min 100% acetonitrile, 25 min 100% acetonitrile, 25.1 min 40% acetonitrile, 30 min 40% acetonitrile.

Sample configuration: about 15 mg of phenethyl isothiocyanate was weighed precisely, and then placed in a 25 ml measuring flask, dissolved with acetonitrile to volume to scale, filtered and injected;

Result:

| Phenylethyl isothiocyanate | Normalized main peak | related substances |
|---|---|---|
| 208 nm | 99.85% | A total of 2 major impurities, accounting for 0.04% and 0.05% respectively |
| 244 nm | 99.92% | One impurity, accounting for 0.08% |

Figures 1, 2:
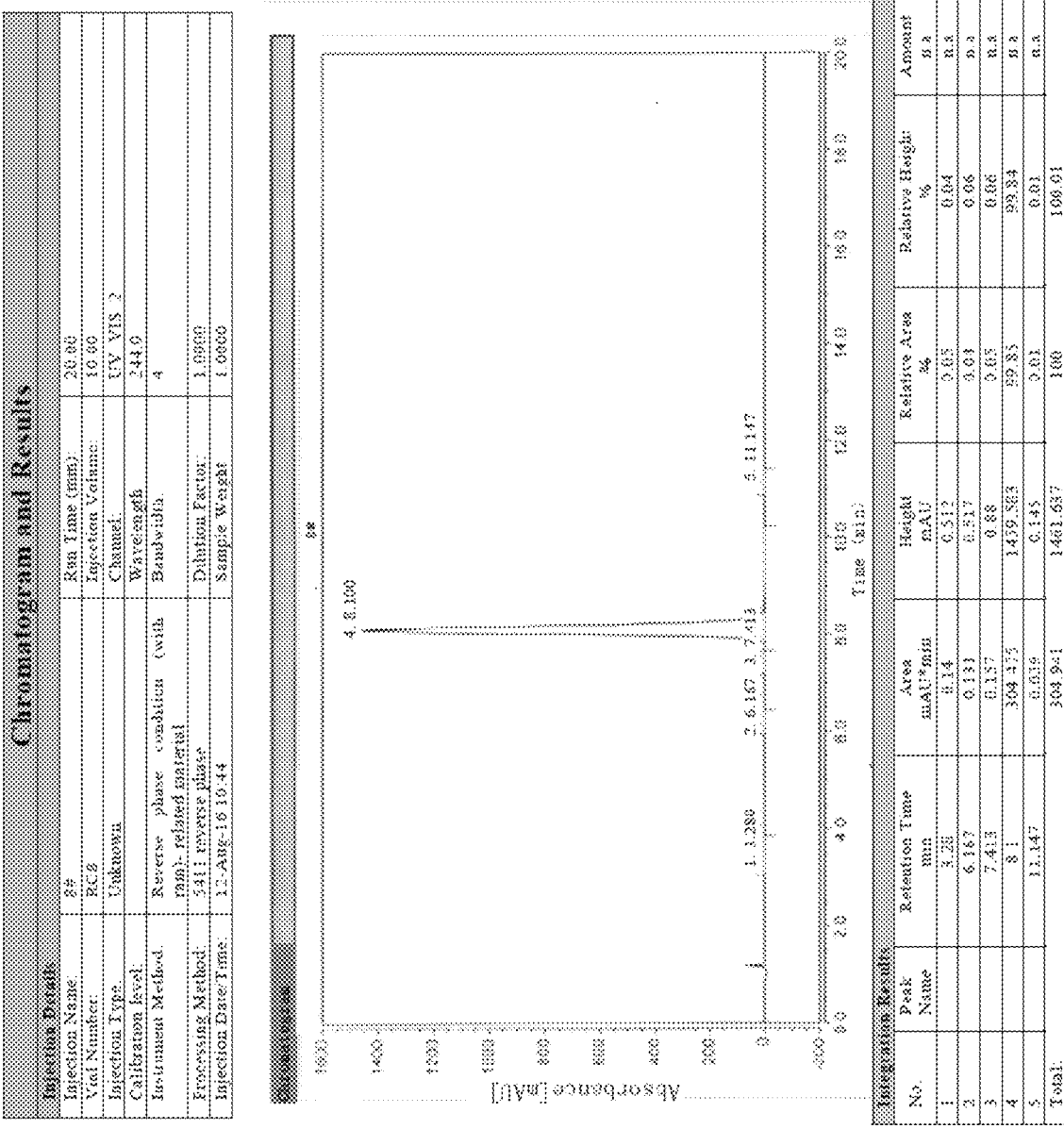
Figure 2:
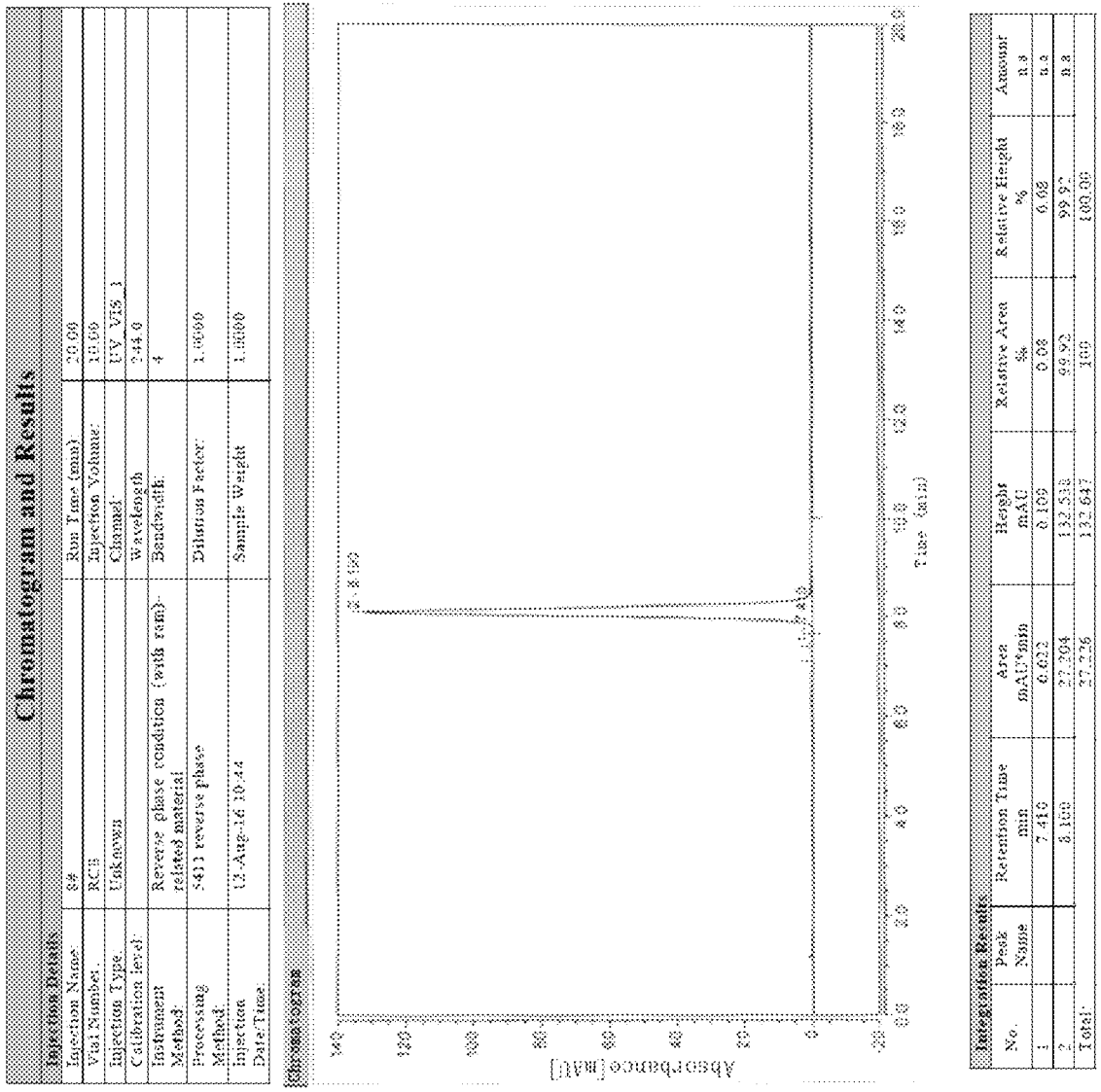

Chromatograms are shown in FIG. 2-1 and FIG. 2-2.

Example 3 Preparation of Allyl Isothiocyanate

Figure 3:
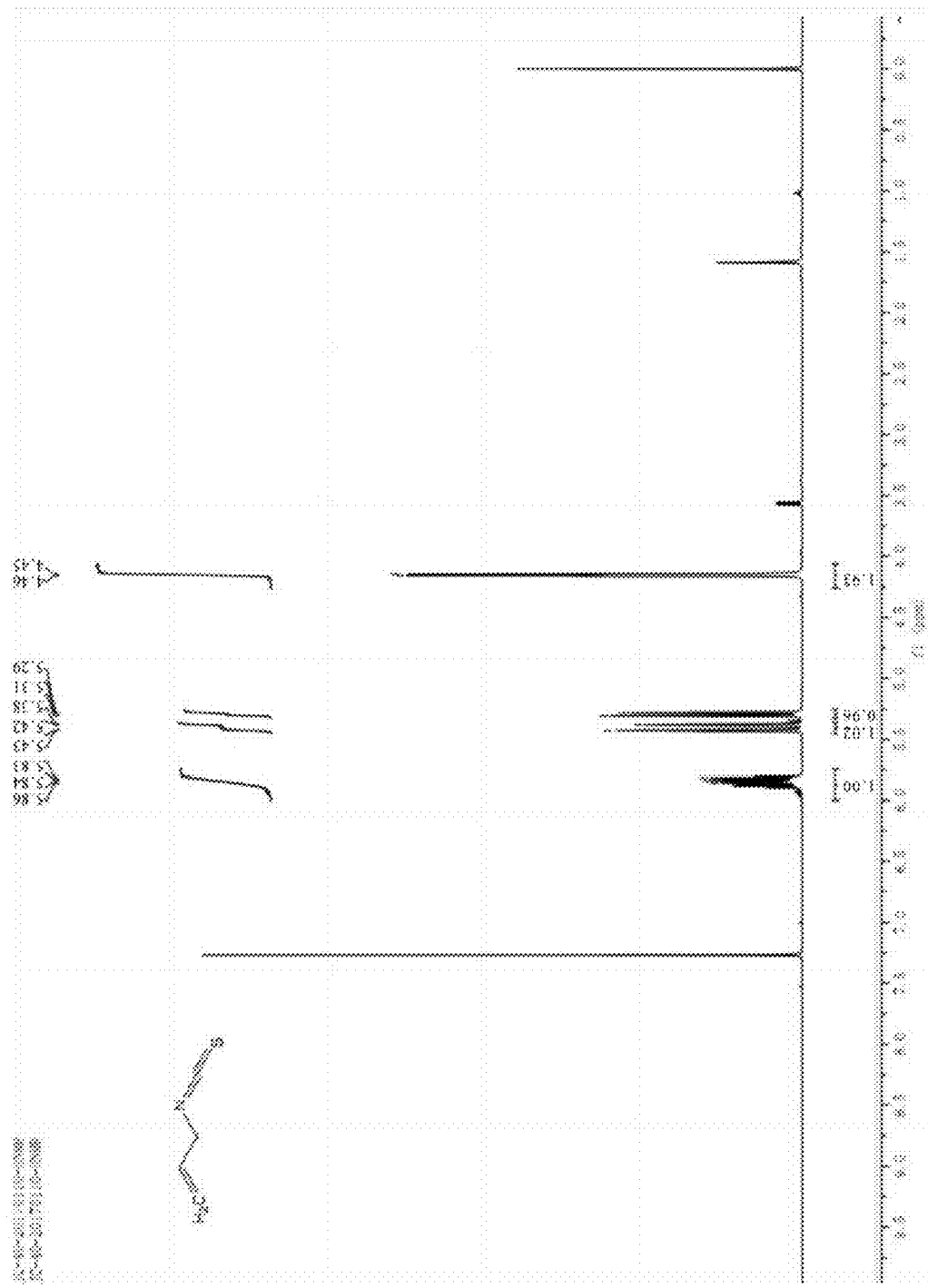
FIG. 3: the structure-confirmation $^1$H NMR pattern of allyl isothiocyanate.

Allylamine (300.0 g, 5.25 mol), triethylamine (743.0 g, 7.34 mol), CS$_2$ (718.9 g, 9.45 mol), BOC anhydride (1134.1 g, 5.20 mol) and 0.18 g of DMAP (0.06 of the amount of allylamine) %) and 1800 ml of ethyl acetate were subjected to the reaction and post-processing purification in the same manner as in Example 1, and finally obtained a pure product. The structure was confirmed in FIG. 3.

Figure 4:
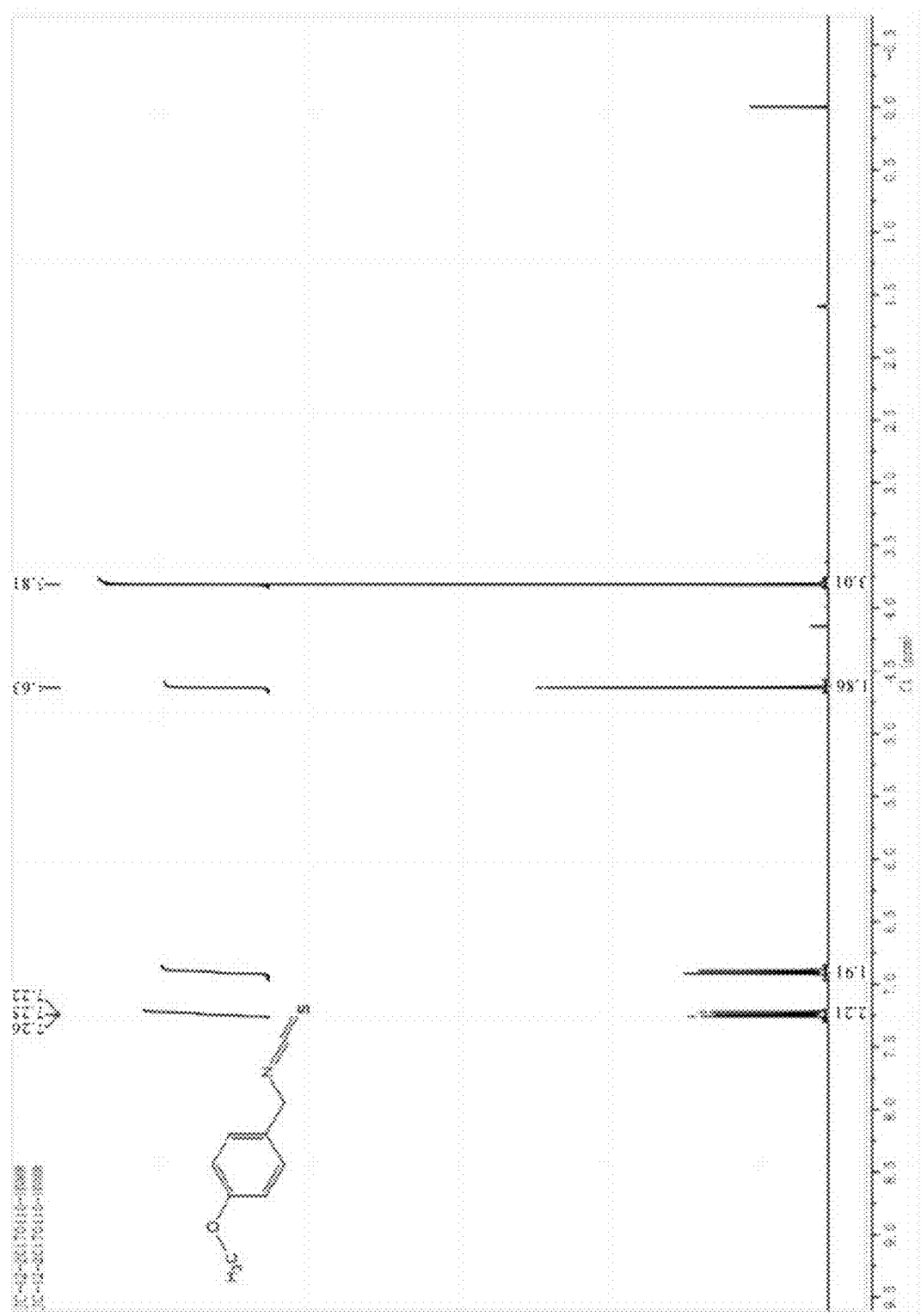
FIG. 4: the structure-confirmation $^1$H NMR pattern of methoxy isothiocyanate.

Example 4 Preparation of 4-Methoxybenzyl Isothiocyanate 4-methoxybenzylamine (300.0 g, 2.19 mol), triethylamine (309.2 g, 3.06 mol), CS$_2$ (299.2 g, 3.93 mol), BOC anhydride (471.9 g, 2.16 mol), 0.18 g of DMAP (0.06% of the amount of allylamine) and 1000 ml of ethyl acetate were subjected to the reaction and post-processing purification in the same manner as in Example 1, and finally obtained a pure product. The structure was confirmed in FIG. 4.

Figure 5:
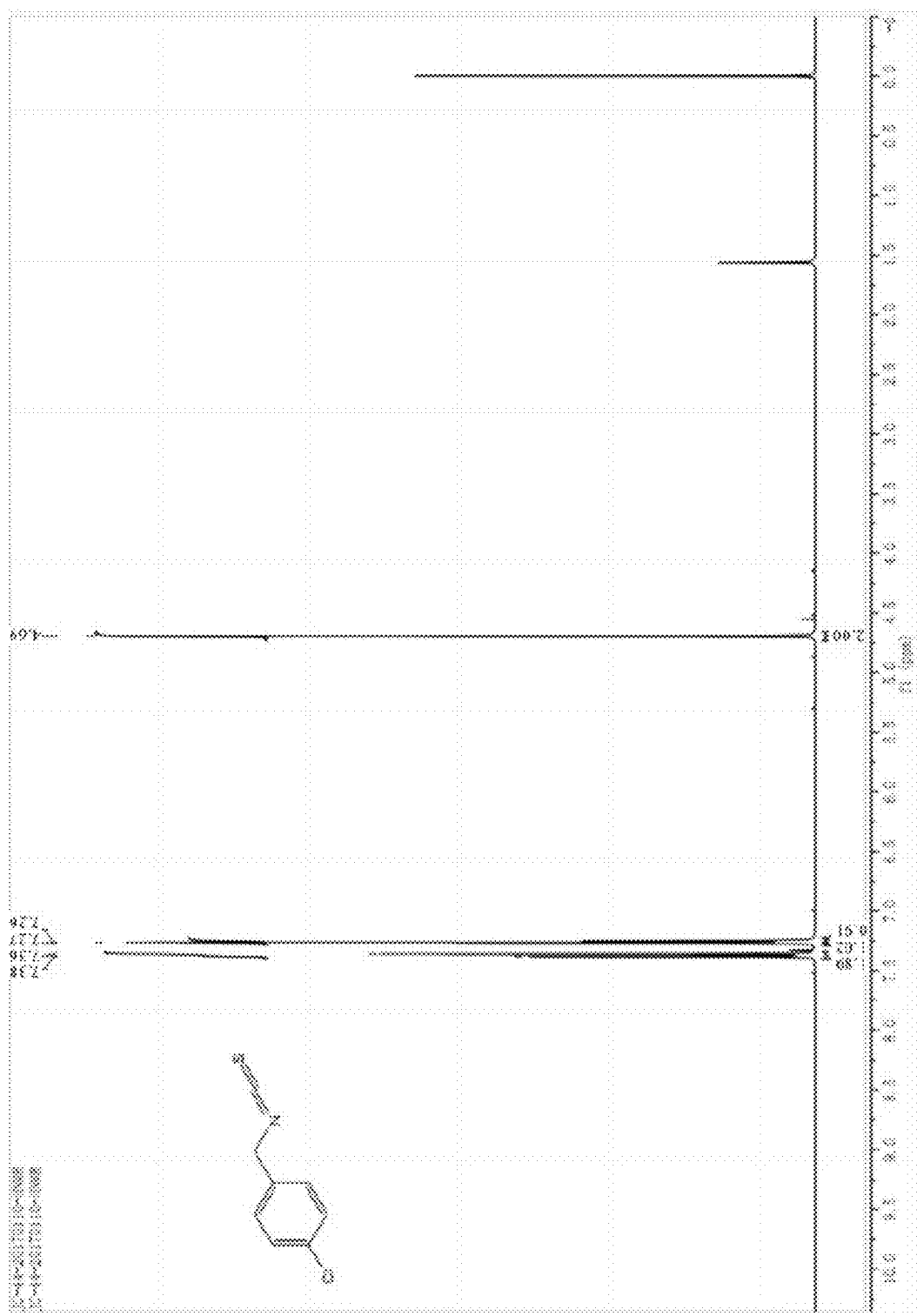
FIG. 5: the structure-confirmation $^1$H NMR pattern of 4-chlorobenzyl isothiocyanate.

Example 5 Preparation of 4-Chlorobenzyl Isothiocyanate 4-chlorobenzylamine (300.0 g, 2.12 mol), triethylamine (299.6 g, 2.96 mol), CS$_2$ (289.8 g, 3.81 mol), BOC anhydride (457.2 g, 2.10 mol), 0.18 g of DMAP (0.06% of the amount of allylamine) and 900 ml of ethyl acetate were subjected to the reaction and post-processing purification in the same manner as in Example 1, and finally obtained a pure product. The structure was confirmed in FIG. 5.

Example 6 Preparation of Ethyl Isothiocyanate

Figure 6:
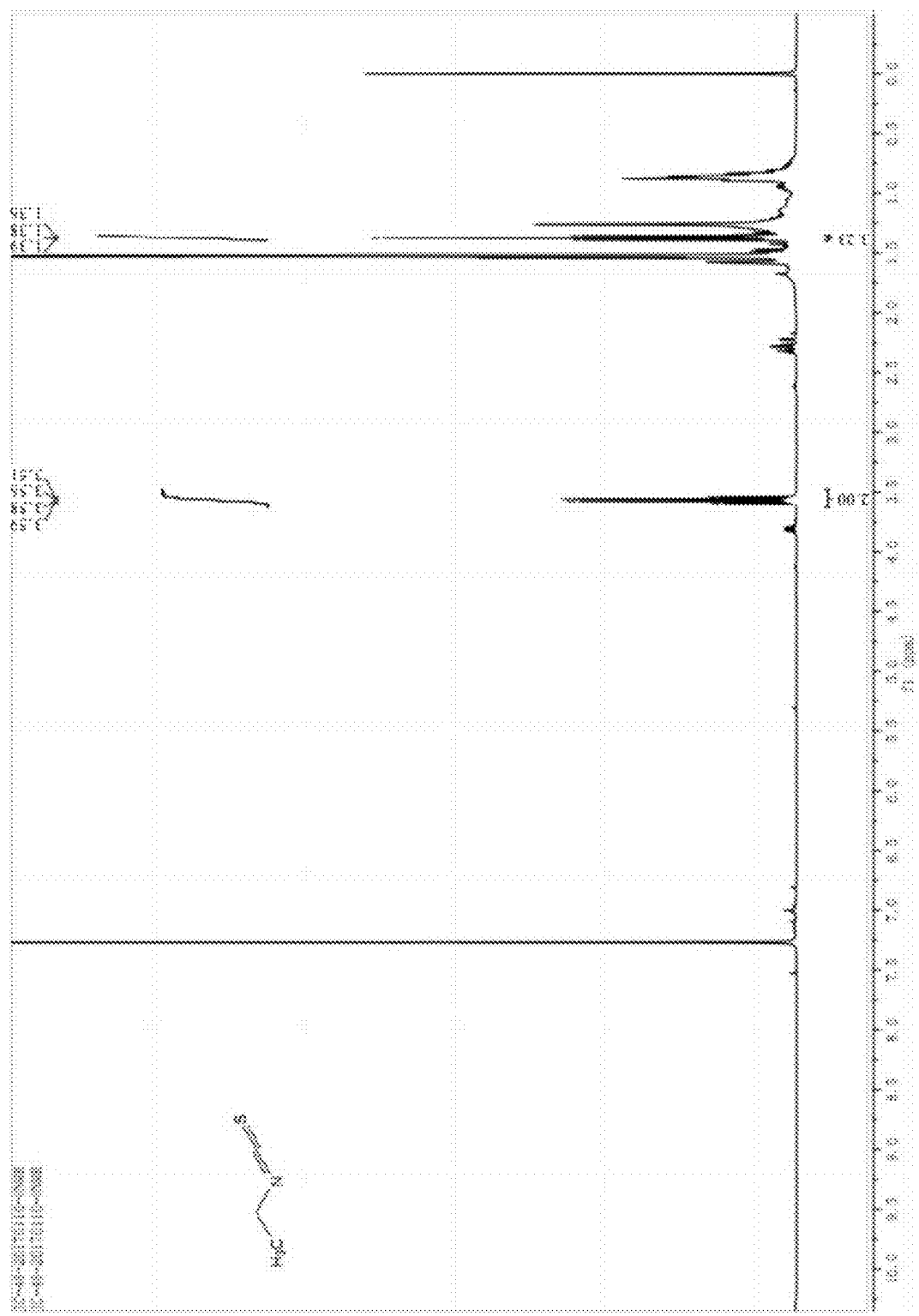
FIG. 6: the structure-confirmation $^1$H NMR pattern of ethyl isothiocyanate.

Ethylamine (300.0 g, 6.65 mol), triethylamine (940.9 g, 9.30 mol), CS$_2$ (910.4 g, 11.96 mol), BOC anhydride (1436.2 g, 6.58 mol), 0.18 g of DMAP (0.06% of the amount of allylamine) and 2300 ml of acetic acid were subjected to the reaction and post-processing purification in the same manner as in Example 1, and finally obtained a pure product. The structure was confirmed in FIG. 6.

Example 7 Industrial Production Equipment Flow Chart

Figure 7:
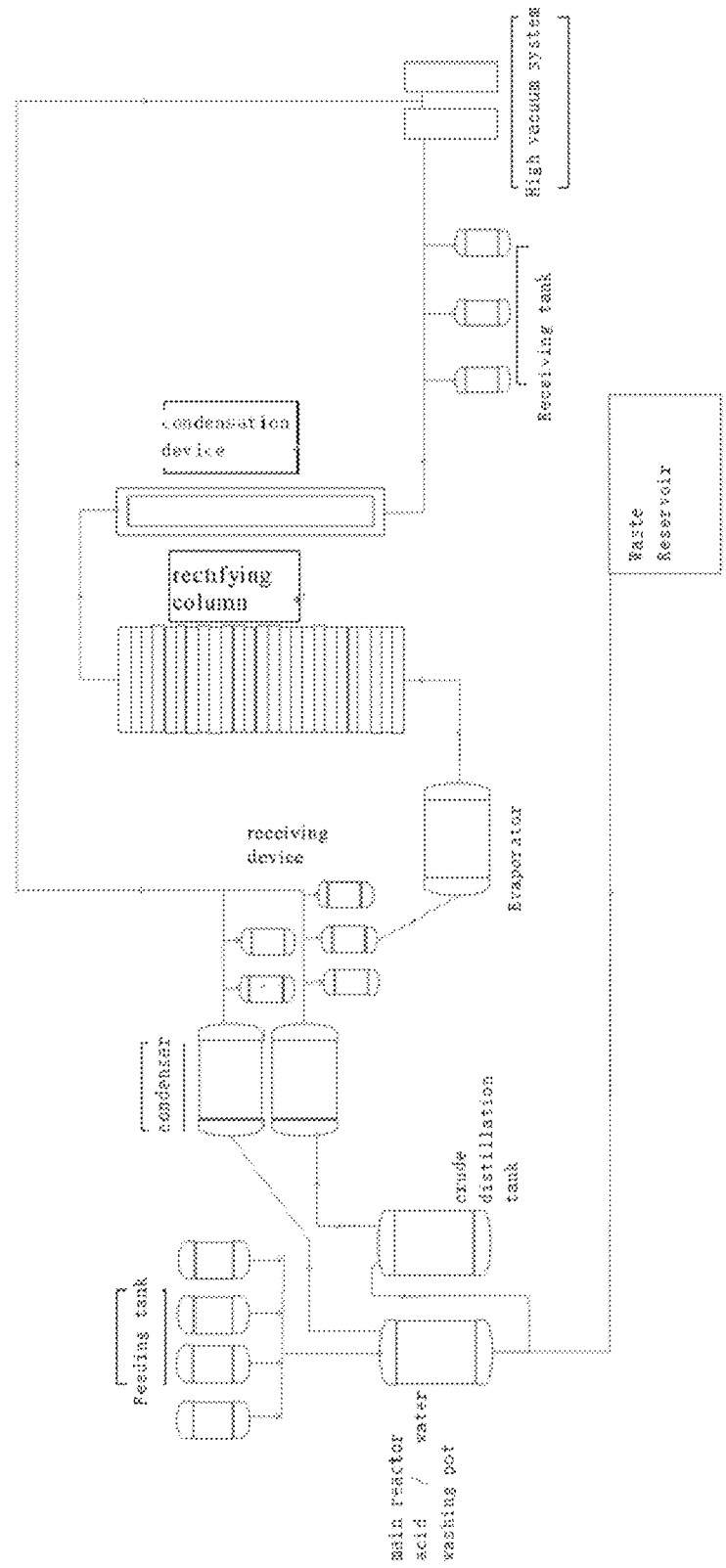
FIG. 7: Flow chart of industrial production equipment.

The equipment flow chart for industrial production was detailed in FIG. 7, wherein the equipment mainly comprised a main reactor, a crude distillation tank located downstream of the main reactor, and a rectifying column.

The main reactor was used to carry out main reaction, acidic water washing reaction and concentration operation, and the equipment further comprises a first condensation and receiving device connected to the upper portion of the main reactor.

The crude distillation tank was used to distill the concentrated product to obtain a crude distillation product. The crude distillation product passed through the second condensation and receiving device to enter into the evaporator and the rectification column from the tail end. The rectifying column was used for rectifying the crude distillation product.

The equipment also includes one or more feeding tanks connected to the main reactor, and located upstream of the main reactor.

All literature mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A method for preparing an isothiocyanate compound of formula (I),

A-N=C=S    (I)

in formula I:
—N=C=S is isothiocyanate group;
A is —XR$_1$ or —CR$_2$R$_3$R$_4$, wherein
X is —(CH$_2$)$_n$—, and n is an integer of 0-6;
R$_1$ is selected from the group consisting of methyl, tert-butyl, isopropyl, methylthio, methoxy, allyl, methallyl, cyclohexyl, methylsulfinyl, naphthyl, methyl cyclohexyl, morpholinyl, diethylamino, benzoyl, ethoxycarbonyl, tert-octyl, chlorine, trimethylsilyl, substituted or unsubstituted phenyl;
wherein, one or more hydrogen in the substituted phenyl are substituted by substituents selected from the following group: halogen, methyl, bromomethyl, ethyl, methoxy, nitro, azido, trifluoromethyl, difluoromethoxy, methylthio, cyano, trifluoromethoxy, trifluoromethylthio, tert-butoxycarbonyl, and ethoxycarbonyl;
$R_2$, $R_3$, and $R_4$ are each independently H, phenyl or $C_{1-3}$ alkyl;
wherein the method comprises:
(1) reacting, in the presence of an organic base, A-$NH_2$ with $CS_2$ in organic solvent so as to obtain a first reaction mixture containing dithiocarbamate, wherein the organic solvent is an ethyl acetate, and ratio of the A-$NH_2$ to the $CS_2$ is 1:1.05-2;
(2) adding, in the presence of an optional base catalyst, a desulfurizing agent to the first reaction mixture to carry out a desulfurization reaction so as to obtain a second reaction mixture containing the isothiocyanate compound of formula (I), wherein the desulfurizing agent is selected from the group consisting of methyl chloroformate, p-toluenesulfonyl chloride, solid phosgene, elemental iodine, chlorosilane, chlorophosphate, dicyclohexylcarbodiimide, dicyandiamide, triphenylphosphine, di-tert-butyl dicarbonate, cyanuric chloride, or combinations thereof;
(3) purifying the second reaction mixture by post-processing to obtain the isothiocyanate compound of formula (I); wherein in (3), the post-processing comprises:
washing the second reaction mixture and concentrating so as to obtain an acid-washed crude product;
distilling the acid-washed crude product so as to obtain a distilled crude product containing the isothiocyanate compound of formula (I); and
subjecting the distilled crude product to rectification under vacuum so as to obtain a pure isothiocyanate compound of formula (I).

2. The method of claim 1, wherein in (1), the organic base is selected from the group consisting of triethylamine, trimethylamine, diisopropylethylamine, triethylene diamine, pyridine, 4-N,N-dimethyl pyridine, potassium t-butoxide, sodium methoxide, sodium ethoxide, hydroxylamine, 3-methylpyridine, pyrrole, or combinations thereof.

3. The method of claim 1, wherein in (2), the desulfurizing agent is di-tert-butyl dicarbonate.

4. The method of claim 1, wherein in (2), the base catalyst is selected from the group consisting of triethylamine, triethylene diamine, pyridine, 4-dimethylamiopryidine, or combinations thereof.

5. The method of claim 1, wherein in (1),
a ratio of the A-$NH_2$ to the organic base is 1:0.5-5, and
a mass volume ratio of the A-$NH_2$ to the ethyl acetate is 10-25%; and
in (2), ratio of the A-$NH_2$ in (1) to the desulfurizing agent is 1:0.9-5.

6. The method of claim 1, wherein in (1), ratio of the A-$NH_2$ to the organic base is 1:0.8-3 and
a mass volume ratio of the A-$NH_2$ to the ethyl acetate is 10-25%; and
in (2), a ratio of the A-$NH_2$ in (1) to the desulfurizing agent is 1:0.9-2, and/or
when the base catalyst is present, mass ratio of the base catalyst to the A-$NH_2$ in (1) is 0.01-2 wt %.

7. The method of claim 1, wherein in (1), ratio of the A-$NH_2$ to the organic base is 1:0.9-2 and
mass volume ratio of the A-$NH_2$ to the ethyl acetate is 10-25%; and
in (2), ratio of the A-$NH_2$ in (1) to the desulfurizing agent is 1:0.95-1.5, and/or
when the base catalyst is present, mass ratio of the base catalyst to the A-$NH_2$ in (1) is 0.05-1 wt %.

8. The method of claim 1, wherein in (3), the distilling is a reduced pressure distilling; and
wherein the washing comprises: washing with an acid solution, wherein molar ratio of a total amount of the acid in the acid solution to the organic base in (1) is 0.8-5:1, calculated as monobasic acid and monobasic base.

9. The method of claim 8, wherein a molar ratio of a total amount of the acid in the acid solution to the organic base in (1) is 0.9-2:1.

10. The method of claim 9, wherein a molar ratio of a total amount of the acid in the acid solution to the organic base in (1) is 1-1.5:1.

11. The method of claim 1, wherein the post-processing comprises one or more characteristics selected from the group consisting of:
the rectification under vacuum is a continuous rectification or a batch rectification;
a rectifying column used for the rectification adopts a structured packing or a random packing; and
a rectified packing material used for the post-processing purification is selected from the group consisting of a stainless steel, a plastic, a glass, a ceramic, or combinations thereof.

12. The method of claim 11, wherein the structured packing is selected from the group consisting of a corrugated packing or a grid packing; and the random packing is selected from the group consisting of a Pall ring packing, a Raschig ring packing, a flat ring packing, a cascade packing ring, an intalox saddles packing, an octagonal ring packing, a conjugate ring packing, a Teller Rosette packing, a HY-PAK packing, a Dixon ring packing, a Cannon ring packing, a Triangular spiral ring packing, a spherical packing, and a combination thereof.

13. The method of claim 11, wherein the rectified packing material is selected from the group consisting of the stainless steel, the ceramics, or combinations thereof.

14. The method according to claim 8, wherein in the reduced pressure distilling, a reflux ratio of a front fraction is 99:1-1:99;
a reflux ratio of a middle fraction is 99:1-1:99; and
a reflux ratio of a post-fraction is 99:1-1:99.

* * * * *